United States Patent
Ramana et al.

(10) Patent No.: US 10,668,113 B2
(45) Date of Patent: *Jun. 2, 2020

(54) FORMULATION FOR TARGETING CANCER IN HUMANS AND CANINES USING VENOM

(71) Applicants: Vivekananda Ramana, East Stroudsburg, PA (US); Ralph Salvagno, Hancock, MD (US)

(72) Inventors: Vivekananda Ramana, East Stroudsburg, PA (US); Ralph Salvagno, Hancock, MD (US)

(*) Notice: Subject to any disclaimer, the term of this patent is extended or adjusted under 35 U.S.C. 154(b) by 312 days.

This patent is subject to a terminal disclaimer.

(21) Appl. No.: 15/936,508

(22) Filed: Mar. 27, 2018

(65) Prior Publication Data

US 2018/0280449 A1   Oct. 4, 2018

Related U.S. Application Data

(63) Continuation-in-part of application No. 15/911,075, filed on Mar. 3, 2018.

(60) Provisional application No. 62/503,347, filed on May 9, 2017.

(30) Foreign Application Priority Data

Mar. 31, 2017 (IN) .............. 2017 31011756

(51) Int. Cl.
| | |
|---|---|
| *A61K 35/646* | (2015.01) |
| *A61K 31/704* | (2006.01) |
| *A61K 36/484* | (2006.01) |
| *A61K 31/4525* | (2006.01) |
| *A61K 36/67* | (2006.01) |
| *A61K 31/7048* | (2006.01) |
| *A61K 9/20* | (2006.01) |
| *A61K 36/185* | (2006.01) |
| *A61K 38/17* | (2006.01) |
| *A61K 9/00* | (2006.01) |
| *A61K 36/68* | (2006.01) |
| *A61K 35/00* | (2006.01) |
| *A61K 36/48* | (2006.01) |
| *A61P 29/00* | (2006.01) |
| *A61P 35/00* | (2006.01) |

(52) U.S. Cl.
CPC .......... *A61K 35/646* (2013.01); *A61K 9/0053* (2013.01); *A61K 9/2013* (2013.01); *A61K 9/2068* (2013.01); *A61K 31/4525* (2013.01); *A61K 31/704* (2013.01); *A61K 31/7048* (2013.01); *A61K 36/185* (2013.01); *A61K 36/48* (2013.01); *A61K 36/484* (2013.01); *A61K 36/67* (2013.01); *A61K 36/68* (2013.01); *A61K 38/1767* (2013.01); *A61P 29/00* (2018.01); *A61P 35/00* (2018.01); *A61K 9/0019* (2013.01); *A61K 9/0095* (2013.01); *A61K 9/2018* (2013.01); *A61K 9/2054* (2013.01)

(58) Field of Classification Search
CPC .. A61K 2300/00; A61K 36/185; A61K 36/48; A61K 36/484; A61K 36/67; A61K 36/68; A61K 35/646; A61K 35/644; A61K 36/47; A61K 38/38; A61K 9/0095; A61K 9/2018; A61K 31/4525; A61K 31/704; A61K 31/7048; A61K 38/1767; A61K 9/0019; A61K 9/0053; A61K 9/2013; A61K 9/2054; A61K 9/2068; A61K 2236/15; A61K 2236/39; A61K 2236/51; A61K 2800/28; A61K 2800/412; A61K 2800/884; A61K 8/0245; A61K 8/19; A61K 8/21; A61K 8/24; A61K 8/25; A61K 8/34; A61K 9/08; A61K 9/1617; A61K 9/1623; A61K 9/1652; A61K 9/1664; A61K 9/1682; A61K 9/2004; A61K 9/2009; A61P 35/00; A61P 29/00; A23L 33/105; A61Q 11/00

See application file for complete search history.

(56) References Cited

U.S. PATENT DOCUMENTS

| | | | |
|---|---|---|---|
| 6,689,749 B1 | 1/2004 | Lebrun et al. | |
| 7,833,979 B2 | 11/2010 | Sullivan et al. | |
| 9,708,377 B2 * | 7/2017 | Norton ................ | A61K 39/00 |

* cited by examiner

*Primary Examiner* — Aaron J Kosar
(74) *Attorney, Agent, or Firm* — Joel Douglas

(57) ABSTRACT

The present invention provides formulation/composition comprising phytonutrients with natural chlorotoxins for targeting cancer, infection, inflammation and pain without any side effects and a method for synthesizing the same. The raw materials are cleaned and dried and to prepare coarse powder of 40 mesh size, extracted with solvent (comprising water:alcohol in a ratio of 40:60) in a ratio of 4:1 with overnight soaking. Prior to cold extraction, the mixture is macerated for 4 hours. The mixture is refluxed for 2 hours at 80° C. The addition of ethanol, maceration and refluxing steps are repeated three times and above solvent is added, if required. The residue is checked for complete extraction after every refluxing step. The extract/residue is filtered and concentrated under vacuum. The extract/residue is vacuum tray dried at 70-80° C. for 12 hours. The extract/residue is scraped and dried lumps of the extract/residue are milled. The extract/residue is sieved and packed.

18 Claims, 1 Drawing Sheet

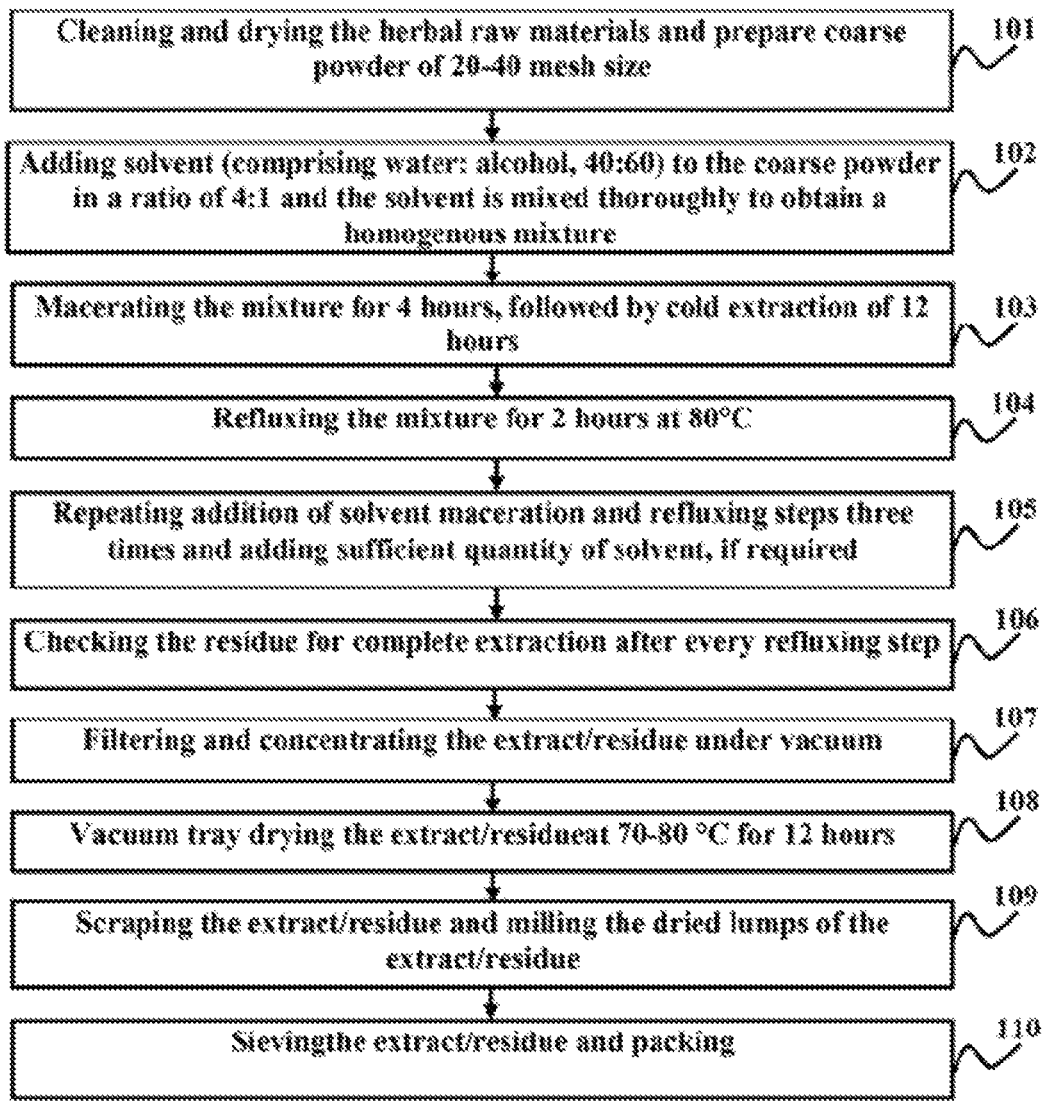

FORMULATION FOR TARGETING CANCER IN HUMANS AND CANINES USING VENOM

CROSS-REFERENCE TO RELATED APPLICATION

This application is a continuation in part of U.S. patent application Ser. No. 15/911,075 filed on Mar. 3, 2018, entitled, A FORMULATION FOR TARGETING CANCER IN HUMANS AND CANINES, This application claims priority from U.S. provisional patent application Ser. No. 62/503,347, filed May 9, 2017, entitled, A FORMULATION FOR TARGETING CANCER IN HUMANS AND CANINES and This application claims priority from Republic of India provisional patent application dated Mar. 31, 2017, Application Number: 2017 31011756, entitled, A FORMULATION FOR TARGETING CANCER IN HUMANS AND CANINES each of which is hereby incorporated by reference herein for all purposes.

STATEMENT REGARDING FEDERALLY SPONSORED RESEARCH OR DEVELOPMENT

The research for patent, "A FORMULATION FOR TARGETING CANCER IN HUMANS AND CANINES," was not funded by any federally sponsored research or development.

FIELD OF DISCLOSURE

The present invention generally relates to the field of herbal extracts and natural compositions, such a scorpion venom from natural source. The present invention, particularly relates to a formulation targeting cancer, infection, inflammation, and pain (analgesics). When used to treat inflammation and pain, the invention results are similar to those achieved by Cyclo-oxygenase-2 (COX-2) inhibitors that are nonsteroidal anti-inflammatory drugs (NSAID) that specifically block COX-2 enzymes and are referred to as COX2 inhibitors. The present invention more particularly relates to a formulation comprising phytonutrients and natural chlorotoxins (about 36 amino acids long) for minimizing tumor growth minimizing secondary metastasis by apoptosis, and inhibition of cancer cell growth. The clorotoxins comprise a mixture of biological chemicals called peptides, that are known to trigger cell death by forming pores in cellular membranes that led to apoptosis. The cell death is useful for targeting tumor cells.

BACKGROUND OF THE INVENTION

Cancer is defined as any of various malignant neoplasia characterized by the proliferation of anaplastic cells. The cancer cells invade the surrounding tissue and metastasize to new sites in the body. Every year, nearly one million new cancer cases are being detected annually in this country. Cancer is the second most common cause of death in the U.S. followed by cardiovascular disease. Cancer accounts for one in every four deaths. The American Cancer Society predicts that in 2017, there would be an estimated 1,688,780 new cancer cases diagnosed and 600,920 cancer deaths in the US. Genetic factors, tobacco, alcohol consumption, foods contaminated with aflatoxins, dietary and behavioral aspects, and chemicals are the main factors that increase cancer risk.

Traditional cancer treatment mainly involves the use of chemotherapy and radiation therapy. There are several side effects of chemotherapy and radiation therapy. The following are various side effects of chemotherapy and radiation therapy: immunosuppression, infections, fatigue, exhaustion (physical, emotional, or mental exhaustion), pain, mouth and throat sores, diarrhea, nausea and vomiting, constipation blood disorders, nervous system weakness, death of healthy cells causing weakness, and anemia.

There is ample evidence for natural formulations being taken into the main stream for the prevention and treatment of the cancer patients, infections, and pain/inflammation. As there are less or no side effects from compositions derived from natural entities, such as plants and arthropods that are members of Arachnids class and order Scorpiones based compounds.

Plants are the mainstay of medicine and credited with mystical and almost supernatural of powers of healing. The ultimate objective of their use is that they should interact directly with physiological chemistry. In recent times the trend of researching new natural or herbal compositions has increased. Further identifying new medicines for the treatment of cancer from natural products is preferred, as the compositions and medications with natural formulations have less or no side effects.

In global platform, herbs have been in use for treating diseases. In modern practice of cancer chemotherapy, several plants derived formulations are routinely used as potent cytotoxic agents. There is immense opportunity for exploring and finding anticancer treatments and natural formulations across veterinary and human application.

The world has seen the use of very promising anti-cancer agents like Taxol, Topotecan, and Periwinkle. The medical literature in India and the traditional system of medicines and classical records provide details of the etiopathogenesis and management of tumors and cancerous conditions. In nature, scorpion chlorotoxins immobilize the envenomated prey. Research has shown that chlorotoxins bind preferentially. It has been shown that certain chlorotoxins will preferentially bind to glioma cells, compared with non-neoplastic cells or normal brain, allowing development of new methods for the treatment and diagnosis of several types of cancer. (*J Neurooncol.* 2005 May; 73(1):1-7, Scorpion venom induces glioma cell apoptosis in vivo and inhibits glioma tumor growth in vitro. By Wang W X[1], Ji Y H.). Notably, scorpions provide a vast opportunity for discovering new chlorotoxins. Scorpions are part of the order Scorpiones and the class Arachnida. They are invertebrates that possess eight legs, and a two-segmented body composed of the cephalothorax and the abdomen. This is the classification of scorpions: Kingdom Animalia (Animals); Phylum: Arthropoda (Arthropods); Subphylum: Chelicerata; Class: Arachnida (Arachnids); and Order: Scorpiones (Scorpions). Current records show that there are 1,004 species known which presents the researcher a wealth of chlorotoxins with which to analyze for effective treatments to disease states such as cancer, alzheimer's, epilepsy, inflammation and pain management. The non-disulfide-bridged scorpion venom peptide has become a crucial substance to initiate pharmacologic activities including antibacterial, antifungal, antimalarial, antiviral and anticancer activities [62, 63]. Effects of Animal Venoms and Toxins on Hallmarks of Cancer Janeyuth Chaisakul[1], Wayne C. Hodgson[2], Sandjaya Kuruppu[2,3], Naiyarat Prasongsook[4] 1. Department of Pharmacology, Phramongkutklao College of Medicine, Bangkok 10400, Thailand, 2. Monash Venom Group, Department of Pharmacology, Biomedical Discovery Institute, Monash University, Clayton, VIC 3800. Australia, 3. Department of Biochemistry & Molecular Biology, Biomedical Discovery Institute, Monash University, Clayton, VIC 3800, Australia, 4. Division of Medical Oncology, Department of Medicine, Phramongkutklao Hospital, Bangkok 10400, Thailand, Chaisakul J, Hodgson W C, Kuruppu S, Prasongsook N. Effects of Animal Venoms and Toxins on Hallmarks of Cancer. *J. Cancer* 2016; 7(11):1571-1578. doi:10.7150/jca.15309. Available from http://www.jcancer.org/v07p1571.htm. These references are hereby incorporated by reference herein for all purposes.

Scorpion Venoms

Chlorotoxin, a 36-amino acid basic peptide from the venom of the scorpion, binds in vitro to medulloblastomas, neuroblastomas, ganglioneuromas, melanomas, pheochromocytomas and small cell lung carcinomas and to mice gliomas. Chlorotoxins have also been effective in targeted radiotherapy of gliomas in mice. Scorpion venom containing chlorotoxins have been used to treat specific cancer tumors.

An example is that Bengalin chlorotoxin, isolated from the Indian black scorpion (*Heterometrus Bengalis Koch*), a large protein chlorotoxin, induces apoptosis in human leukemic cells in vitro. Bengalin also shows efficacy in a rat model of osteoporosis, but exhibits subacute cardiotoxicity. *Toxicon.* 2010 February-March, 55(2-3):455-61. doi: 10.1016/j.toxicon.2009.09.013. Epub 2009 Oct. 2. https://www.ncbi.nlm.nih.gov/pubmed/19800909 Chloride Movements Across Cellular Membranes Zhiwei Cai, . . . David N. Sheppard, in Advances in Molecular and Cell Biology, 2006.

Nature has blessed investigators of cation channels with an armamentarium of peptide toxins to selectively eliminate different types of cation currents. Disappointingly, similar tools have, for a long time, been unavailable to investigators of anion channels. DeBin et al. (1993) purified a 4.1 kDa basic peptide from scorpion venom with sequence similarity to small insectotoxins. Because this peptide inhibited outwardly rectifying Cl− channels reconstituted into planar lipid bilayers, DeBin et at (1993) named this toxin chlorotoxin. Subsequently, Maertens et al. (2000) demonstrated that sub-micromolar concentrations of chlorotoxin were without effect on volume-regulated, Ca2+-activated, and CFTR Cl− channels. Based on their data Maertens et al. (2000) concluded that chlorotoxin is not a general Cl− channel inhibitor.

Peptide toxins have been valuable probes in efforts to identify amino acid residues that line the permeation pathway of cation-selective channels. McCarty et al, in Am J Physiol Cell Physiol. 2004 November; 287(5):C1328-41. Epub 2004 Jul. 7, entitled, Inhibition of CFTR channels by a peptide toxin of scorpion venom. Fuller M D1, Zhang Z R, Cui G, Kubanek J, McCarty N A. searched for peptide toxins that inhibit the CFTR Cl− channel with the aim of identifying new tools to probe CFTR structure and function. In their initial study, Fuller et al. (2004) demonstrated that scorpion venom contains a low-molecular-weight peptide toxin that reversibly inhibits recombinant human CFTR expressed in *Xenopus* oocytes only when applied to the intracellular side of the membrane. Subsequently, Fuller et al. (2005) demonstrated that the peptide toxin preferentially inhibits CFTR when the channel is closed, suggesting that the toxin is a state-dependent blocker of the CFTR Cl− channel. Of note, the off-rate for the interaction of the toxin with CFTR is one hundred times slower than that of glibenclamide (Fuller et al. 2005). This argues well for the purification of a high-affinity peptide blocker of the CFTR Cl− channel.

Looking at Animal Toxins in Biotechnological Applications, as referenced in Animal Toxins, Jean-Marc Sabatier, Michel De Waard, in Handbook of Biologically Active Peptides (Second Edition), 2013, the group of Wonnacott showed that the subcellular distribution of alpha7 nicotinic acetylcholine receptors can be investigated by coupling alpha bungarotoxin to gold nanoparticles. In that respect, toxins seem perfect tools to target anticancer agents directly to the site of tumor in vivo if their targets are overexpressed in tumors. For instance, the G protein-coupled receptors (BBR1, BBR2, and BBR3) of bombesin, a 14 amino acid peptide from frog skin (specifically, the European firebellied toad *Bombina bombina*), are overexpressed in small cell carcinoma of lung, gastric cancer, neuroblastoma 21 and human prostate cancer. This property has been used to prepare bombesin derivatives harboring lutetium-1777 for prostate cancer targeting, in vivo imaging, and therapeutic intervention.24 Another successful example for tumor applications includes chlorotoxin,16,29 a 36-mer peptide with four (4) disulfide bridges initially isolated from the venom of the Israeli scorpion *Leiurus quinquestriatus*. Although initially developed for the diagnosis and treatment of glioma, chlorotoxin specifically labels cancer cells from other solid tumors, as well as melanoma, small cell lung carcinoma, neuroblastoma, medulloblastoma, Ewing's sarcoma, and pheochromacytoma. The identity of the biomarker on which it binds is still under debate (initially a chloride channel, then matrix metalloprotein 2, and now, which seems more probable, annexin 2A). Currently, a 131 iodinated version of the toxin from Eisai (TM601) has successfully ended conical research phase II for the treatment of recurrent glioma and has obtained FDA approval to go to phase III clinical trials. Besides, it has also obtained FDA approval to investigate the effect of TM601 on newly occurring glioma. TM601 is extremely stable, presents no immunogenicity and produces no toxicity in humans. Several derivative molecules (termed TM602, TM604, etc.) have been produced to facilitate phenotyping and histological staining, and patient treatment. The door is now open for use of other toxins in cancer diagnosis and treatment, BmKCT, which presents 68% amino acid sequence identity with chlorotoxin, also targets glioma in vivo and prevent its progression. Similarly, the nontoxic B subunit of the pathogen-produced Shiga toxin known to bind to the glycosphingolipid Gb3 which is overexpressed in some tumors specifically labels human colorectal carcinoma in nude mice.33 Other technological applications are possible with toxins. The 12 amino acid peptide Tet1, derived from tetanus toxin is an efficient vector for the delivery of plasmid DNA in complex to polyethylenimine (22 kDa). A similar fragment of tetanus toxin, when placed in fusion to the reporter protein GFP, allows mapping of synaptic connections of the mammalian central nervous system.

Most animal toxins hit cell surface receptors. This is by far the most straightforward means to interfere with signaling pathways for peptides as these molecular entities are sometimes considered unable to cross the cell plasma membrane. There are many exceptions to this belief, as some animal toxins target intracellular ion channel receptors. This occurs with toxins targeting the ryanodine receptor, an intracellular calcium channel located in the membrane of the endoplasmic reticulum and controls cytosolic Ca2+ release. These toxins present intriguing peptide sequences that efficiently favor their entry into the cytoplasm. Ion channel recognition and cell permeation can easily be dissociated to retain the latter property. Also, cell penetration can be derived for the cell entry of other compounds of pharmaceutical or imaging interests. Nanoparticles potential: types, mechanisms of action, actual in vitro and animal studies, recent patents, Gerardo Caruso, Maria Caffo, in Innovative Brain Tumor Therapy, 2014 4.3.3.

An estimated 40% of clinically approved drugs fall into the category where either the natural compound itself or a modified version is the approved drug. These include statins (found in bacterial secretions) used to lower cholesterol, quinines (found in cinchona trees) as anti-malaria, and paclitaxel (found in yew trees) as anti-cancer medication.

Many of these natural products are toxins produced by plants or animals as a form of defense. And scorpion venom has been gaining interest as a source of new drugs. It contains a mixture of biological chemicals called peptides, some of which are known to trigger cell death by forming pores in biological membranes. Cell death can be useful if we are able to target, say, tumor cells to auto-destruct.

Researchers investigating the use of scorpion venom as a cancer treatment have identified certain chemicals called peptides, contained in the venom, that can help destroy cancer cells and avoid the side effects of chemotherapy and other conventional cancer treatments. The peptide, chlorotoxin, is the same chemical that paralyzes a scorpion's prey. In one study, published in 2015 by *Science Daily*, researchers found that these peptides bind specifically to cancer cells and shrink and destroy them.

These toxins can have very potent effects. For instance, one particular small peptide, known as TsAP-1, isolated from the Brazilian yellow scorpion (*Tityus serrulatus*), has both, anti-microbial and anti-cancer properties. http://www.iflscience.com/health-and-medicine/how-scorpion-venom-could-yield-new-cancer-treatment/.

Additionally, as sited in smithsonian.com, Scorpion Venom is helping treat cancer patients. A potential source of effective chlorotoxins is the venom from Scorpions that are part of the order Scorpiones and the class Arachnida. They are invertebrates that possess eight legs and a two-segmented body composed of a cephalothorax and abdomen. This is the classification of scorpions: Kingdom Animalia (Animals); Phylum: Arthropoda (Arthropods); Subphylum: Chelicerata; Class: Arachnids (Arachnids); and Order: Scorpiones (Scorpions). Current records show that there are 1,004 known species. The number of species and the potential of compounds from the more than 1000 known species combined with the knowledge base of both native American Indian homeopathic medicine and other homeopathic literature indicate that there is a wealth of opportunity in the chlorotox's of scorpion species to elevate the symptoms of effective treatments to disease states such as heart disease, cancer, alzheimer's, epilepsy, inflammation and pain management.

The largest of the scorpion families is the Buthidae with over 800 scorpion species. They live mostly in tropical, subtropical, and partly in temperate habitats, except New Zealand and Antarctica.

Seventy-two scorpion species, belonging to Hemiscorpiidae, are known to inhabit all continents, particularly in tropical and subtropical habitats, with the exception of North America. With respect to the invention and the disclosure of scorpions the following Scorpion family's are include by definition: Bothriuridae, Buthidae, Caraboctonidae, Chactidae, Chaerilidae Diplocentridae, Euscorpiidae, Gigantoscorpionidae, Hemiscorpiidae, Palaeopisthacanthidae, Pseudochactidae, Scorpionidae, Superstitioniidae, Typhlochactidae and Vaejovidae.

Some of the world's largest scorpions belong to Scorpionidae family, which has approximately 240 scorpion species. Included in this family is the emperor scorpion (*Pandinus imperator*), one of the largest scorpion species known. Another giant is the *Heterometrus swammerdami*, which can reach lengths of twenty (20) centimeters.

The large number of venom producing scorpions makes for promising possibilities to find a significant number of pharmaceutical active molecules, because all true scorpion species have venom to kill or paralyze prey. Effects of a scorpion sting vary for humans, since some experience nothing more than a kind of numbness due to the sting, while sensitive individuals can die from the poisonous venom.

For example, in the venom of the *Centruroides tecomanusscorpion* from Colima, a southwest state of Mexico, over a hundred proteins have been found and identified as possessing "possible" toxic effect against cancer cells according to a scientific study. In preliminary investigations, researchers have identified peptides (amino acid molecules) that destroy cancer cells in vitro by binding to cancer cells and causing death of the cancer cell.

Research to date shows that natural based formulations especially designed from natural phytonutrients and natural chlorotoxins can be used for targeting cancer, heart disease, alzheimer's, epilepsy, inflammation and pain management.

Hence, there is need for a formulation comprised of promising natural based formulations, especially phytonutrients and natural chlorotoxins, for targeting cancer and with less or no side effects. Also, there is a need for a method for synthesizing the formulation comprising phytonutrients and natural chlorotoxins for cancer indications.

Hence, there is a needed for a formulation comprised of natural based formulations, especially phytonutrients and natural chlorotoxins for targeting cancer, heart disease, alzheimer's, epilepsy.

Also there is a needed for a formulation comprised of promising natural based formulations, especially phytonutrients and natural chlorotoxins, for targeting inflammation and pain management.

BRIEF SUMMARY OF THE INVENTION

The present disclosure provides various embodiments of the present invention. The embodiments provide a formulation/composition comprising phytonutrients and natural chlorotoxins for targeting cancer without any side effects. The embodiments of the present invention also provide a method for the synthesis of a formulation comprising phytonutrients including *Cannabis sativa* (cannabinoids), *cannabis indica* and natural chlorotoxins for targeting cancer, inflammation, pain, and infection (as discussed in Mediators of Inflammation Volume 2010 (2010), Article ID 903295, http://dx.doi.org/10.1155/2010/903295, Scorpion Venom and the Inflammatory Response by Vera L. Petricevich)

According to one embodiment of the present invention, the formulation or composition comprising phytonutrients and natural chlorotoxins for targeting cancer is referred as "RX002CxN".

According to one embodiment of the present invention, the formulation/composition (RX002CxN) comprises water/alcohol (40:80) solvent extracts of *Glycyrriza glabra, Piper longum, Picrorhiza kurroa, Phyllanthus amarus, Bauhinia variegate,* and *Terminalia chebula* in predetermined amounts in addition with the natural chlorotoxins derived from scorpion venom.

According to one embodiment of the present invention, the method for synthesizing the formulation/composition (RX002CxN) comprising phytonutrients selected from the group of phytonutrients bearing plants comprising of *Glycyrriza glabra, Piper longum, Picrorhiza kurroa, Phyllanthus amarus, Bauhinia variegate,* and *Terminalia chebula* and natural chlorotoxins such as Blue Scorpion Venom Chlorotoxin for targeting cancer, comprises the following steps. The herbal raw materials are cleaned and dried and combined to form a uniform mixture. Then a coarse powder is prepared such that it can pass through a 20-40 mesh size by either grinding or pulverizing using a suitable tool such as a mortar and pestle or a processor such as a IKA Handheld Analytical Mill or an IKA Continuous Feed Grinding machine EW-04300-30 with IKA 2836001 Continuous feed grinding drive. Then solvent comprising water/alcohol in a ratio 40:60 is added to the coarse powder mixture in a ratio 4-parts powder and 1-part solvent and the solvent is mixed thoroughly to obtain a homogeneous mixture. The mixture is macerated for at least 4 hours to 12 hours followed by a cold extraction of 12 hours. Cold extraction is achieved by taking the homogeneous mixture of solvent and phytonutrients powder and dissolving the mixture in warm water and then rapidly cooling the mixture. The insoluble compounds precipitate out of the water, while the soluble ones stay dissolved. The solution can then be separated by reflux, filtration, or decantation. In the preferred method, the mixture is refluxed for 2 hours at 80° C. The addition of solvent maceration and refluxing steps are repeated a minimum of three times and each time sufficient quantity of solvent is added, if required. The residue is checked for complete extraction after every refluxing step. The extract from the residue is filtered and concentrated under vacuum. The extract from the residue is vacuum tray dried at 70-80° C. for 12 hours. The extract from the residue is scraped and the dried lumps of the extract from the residue are milled. The natural chlorotoxin is added to the extract/residue and blended homogenously. The extract/residue sieved and packed. The percentage yield is calculated according to the weight of the raw materials. The example utilizes the Blue Scorpion Venom Chlorotoxin venom however the opportunity to expand the viable chlorotoxin pool of compounds by utilizing any one of the more than 1004 known species of scorpion's in the treatment of disease's such as heart disease, cancer, aizheimer's, epilepsy, inflammation and pain management is incorporate because any one of the vast number of scorpion's could be used as a donor animal and this specification includes the incorporation of any of these animals being used as an alternative sources of chlorotoxins. For this example the Blue Scorpion Venom Chlorotoxin venom is extracted by a mild electro-stimulation method, that includes stimulating and scorpion restraining devices. However, researchers have had success milking scorpions in the Buthidae family, the Scorpionidae family which includes the emperor scorpion (*Pandinus imperator*), and the the *Heterometrus swammerdami* scorpion as well as specific species such as African *Androctonus australis, Hadrurus hirsutus*, Albino Scorpions, Black Scorpions or Asian Forest Scorpions, Blue Scorpions, Emperor Scorpions, Deathstalker Scorpions, Lesser Brown Scorpions, Red Claw Scorpions, Red Scorpions, Sand Scorpions, Tailless Whip Scorpions and Whip Scorpions.

Once the venom is extracted, it is frozen and then lyophilized into a powder form that is added to the phytonutrients powder in the ratio 1 part venom 10,000 parts by weight phytonutrients extract, then mixing thoroughly. The 1 part venom to 10,000 parts phytonutrients extract is preferred for canines and small animals. However, clinically effective powders with ratios from 1 to 1000 parts venom and 1000 to 20000 parts by weight phytonutrients extract have been made successfully. The finished powder is then made into a nutraceutical supplement in the form of pills that are taken by the patient. The pills can also contain any buffering or inorganic compounds suitable for the pill formation and that does not adversely affect the finished powder of phytonutrients extract and chlorotoxin powder. Typical excipients can be found in Table 1. However, the final nutraceutical supplement could be formulated into a number of suitable delivery means such as injectable oral tablet, oral liquid topical cream, nasal spray, dry powder aerosols, powder structures for water-soluble drugs, and powder containing time release capsules, since dry powder aerosols is the best route reported for chlorotoxin to cross the blood brain barrier and reach its site: in cases of glioma, this may be a preferred formulation. All pharmaceutical formulations of the venom will be taken as a base in a suitable physiological vehicle to which the processed phytonutrient ingredients will be added and formulated with other inert excipients, stabilizers, and preservatives, as needed. The oral liquid and injectable formulations can be formed by taking the powder of phytonutrients extract and chlorotoxin powder and mixing it with a carrier liquid, wherein the carrier liquid is selected from the group consisting of deionized water, saline, plasma, and interstitial fluid, as well as stabilizers and preservatives, as needed. The injectable formulations commonly use chemicals used in the production of vaccines. These include suspending fluid (sterile water, saline, or fluids containing protein); preservatives for example (Benzoic acid, salts, Sorbic acid, Parabens and paraben substitutes such as natural products such as "grape fruit seed", Benzyl Alcohol, Phenoxyethanol, Sodium Benzoate, Potassium Sorbate) and stabilizers (for example, albumin, phenols, and glycine); and adjuvants or enhancers that help improve the injectable effectiveness. The adjuvants can be selected from the group consisting of aluminum phosphate, aluminum hydroxide, Docosahexaenoic acid, and MF59, an immunologic adjuvant that uses squalene. The oral formulations utilize stabilizers selected from polyols, albumins and other proteins, surfactants, poloxamers, cyclodextrins and preservatives selected from Benzoic acid, salts, Sorbic acid, Parabens and paraben substitutes such as natural products such as "grape fruit seed", Benzyl Alcohol Phenoxyethanol, Sodium Benzoate, Potassium Sorbate). The oral formulations utilize preservatives selected from the group Methyl, ethyl, propyl parabens, sodium benzoate, benzoic acid, Methyl paraben/sodium benzoate, Benzyl Alcohol, Phenoxyethanol, Sodium Benzoate, Potassium Sorbate and suitable combinations.

The pharmaceutical formulations of the present invention provide a formulation/composition comprising phytonutrients and natural chlorotoxins for targeting cancer in humans, felines and canines, and other pet animals without any side effects.

According to one embodiment of the present invention, the formulation/composition (RX002CxN) has cytotoxic activity that induces apoptosis on a variety of cancer cells. The apoptosis is induced by a pattern of DNA fragmentation and regulation of the phosphorylation that affects the p53 tumor suppressor protein. The activation of the p53 protein leads to cell cycle arrest, and provokes apoptotic cell death. The process of phosphorylation increases the expression of protein (p27). The protein, p27 is an inhibitor of cyclin-dependent complexes. The formulation comprising phytonutrients and natural chlorotoxins prevents angiogenesis, reduces growth, cell division, and metastasis through apoptosis, leading to the death of cancer cells.

According to one embodiment of the present invention, the main compounds of formulation/composition (RX002CxN) are a mixture of glycyrrhizic acid (13% on d/b), piperine (0.54% on d/b), picroside and kutikoside (15% d/b), bitters (12% d/b), tannins (55% d/b-78% d/b), and a peptide comprising 36 amino acids.

According to one embodiment of the present invention, the compounds of formulation/composition (RX002CxN) induce regulation and inhibition of the potassium (K+) 3-4 kDa, sodium (N+) 6-8 kDa, and chloride (Cl+) ionic channels. The regulation of the potassium (K+) 3-4 kDa and sodium (N+) 6-8 kDa volt-gate ion channels of tumor cells leads to cell cycle arrest and programmed cell death. The complex of a peptide comprising 36 amino acids has a high positive charge at pH 7, allowing for preferential binding to abnormal cancer cells and leaving the normal cells intact. By forming multiple links with proteins on the surface of the cell membrane of malignant neoplasms, the cancer cells lose their external receptors and their ability to penetrate healthy undamaged tissues. Thus the formulation or composition (RX002CxN) comprising phytonutrients and natural chlorotoxins prevent tumor metastasis. The components of RX002CxN arrest the cancer cells in the G1 phase of the cell cycle, due to changes in mitogenic signals specific to malignant cells. This leads to a universal effect on many cancer types.

According to one embodiment of the present invention, the formulation or composition (RX002CxN) comprising phytonutrients and natural chlorotoxins has the ability to function as a transport mechanism. The formulation or composition (RX002CxN) intensifies the binding preferences with malignant cells and increases the delivery of the main compounds into cancer cells by 58%. The delivery of the main compounds of the formulation or composition increases the effectiveness of RX002CxN composition/formulation, when compared to the other non-standardized formulation.

According to one embodiment of the present invention, the main compounds are the 'phyto-complex with chlorotoxins'. The phyto-complex comprises the extracts of *Glycyrriza glabra, Piper longum, Picrorhiza kurroa, Phyllanthus amarus, Bauhinia variegate*, and *Terminalia chebula* in predetermined amounts. The chlorotoxins used in the composition are derived from the polypeptide of the scorpions' venom. An example is the blue scorpion venom. This 'phyto-complex with natural chlorotoxins' acts as potent anti-cancer composition, and is active against multi-focal oncological usages with special attention of cancers of blood, bone, colon, cervix, bladder, ovary, breast, prostate, and uterus.

According to one embodiment of the present invention, the cancerous cells have more negative charges on their cell surface, higher intracellular sodium, and lower intracellular concentrations of potassium, magnesium, and calcium. These abnormalities result in cancer cells having lower trans-membrane potentials than normal cells and altered membrane permeability. These cell membrane changes in cancer cells interfere with the flow of oxygen and nutrients into the cells and impair aerobic metabolism causing cancer cells to rely more on anaerobic metabolism for energy production. The anaerobic metabolism, excessive sodium concentrations, low trans-membrane potential, and pH alterations create the abnormal intracellular conditions of cancer cells.

According to one embodiment of the present invention, the highly increased extracellular positive charges by the specialized formulation/composition (RX002CxN) accelerate reduction in growth in malignant cells which is essential in the cell death of malignant cells.

According to one embodiment of the present invention, the absorption of the formulation or composition (RX002CxN) starts in the duodenum (the first section of the small intestine in higher vertebrates). The peptides, proteins and minerals of the formulation or composition (RX002CxN) are completely absorbed quickly and easily by the human body, within 20 minutes. The main compound of the formulation or composition (RX002CxN), a 36 amino acids peptide, passes the blood brain barrier and inhibits glioma cell invasion. The formulation or composition (RX002CxN) has a cumulative effect, in most cases needing only 24 hours to have a full effect.

According to one embodiment of the present invention, the main compounds present in the anti-cancer formulation or composition (RX002CxN) are the 'phyto-complex with natural chlorotoxins'. The phyto-complex comprises the extracts of *Glycyrrizaglabra, Piper longum, Picrorhiza kurroa, Phyllanthus amarus, Bauhinia variegate*, and *Terminalia chebula* in predetermined amounts. The chlorotoxins used in the composition are derived from the polypeptide of the blue scorpion saliva. This 'phyto-complex with natural chlorotoxins' acts as a potent anti-cancer composition and is active against multi-focal oncological usages with special attention to cancers of blood, bone, colon, cervix, bladder, ovary, breast, prostate, inflammation, pain, infection, and uterus.

The primary objective of the present invention is to provide a formulation comprising phytonutrients and natural chlorotoxins for targeting cancer without any or less side effects.

Another objective of the present invention is to provide a method for the synthesis of a formulation comprising phytonutrients with natural chlorotoxins for targeting cancer.

Yet another objective of the present invention is to provide a formulation comprising phytonutrients with natural chlorotoxins for inhibition and minimizing the tumor growth.

Yet another objective of the present invention is to provide a formulation comprising phytonutrients with natural chlorotoxins for minimizing secondary metastasis by apoptosis of variety of cancer cells by a pattern of DNA fragmentation.

Yet another objective of the present invention is to provide a formulation comprising phytonutrients with natural chlorotoxins for arresting cancer cell growth.

Yet another objective of the present invention is to provide a formulation comprising phytonutrients with natural chlorotoxins for prevention of angiogenesis in cancer cells.

Yet another objective of the present invention is to provide a formulation comprising phytonutrients with natural chlorotoxins for effective treatments to disease states such as cancer, Alzheimer's disease, epilepsy, inflammation and pain management.

Yet another objective of the present invention is to provide a formulation comprising phytonutrients and natural chlorotoxins for regulating the process of phosphorylation that affects the p53 tumor suppressor protein leading to cell cycle arrest and apoptotic cell death.

Yet another objective of the present invention is to provide a formulation comprising phytonutrients and natural chlorotoxins for arresting the growth of cancer cell in the G1 phase of the cell cycle, changing in mitogenic signals specific to malignant cells and providing a universal effect on different forms of cancer.

Yet another objective of the present invention is to provide a formulation comprising phytonutrients and natural chlorotoxins for targeting cancer in humans, felines, canines, and other pet animals.

The primary objective of the present invention is to provide a formulation comprising phytonutrients and natural chlorotoxins for targeting cancer with no or less side effects.

Another objective of the present invention is to provide a method for the synthesis of a formulation comprising phytonutrients with natural chlorotoxins for targeting cancer.

Yet another objective of the present invention is to provide a formulation comprising phytonutrients with natural chlorotoxins for inhibition and minimizing the tumor growth.

Yet another objective of the present invention is to provide a formulation comprising phytonutrients with natural chlorotoxins for minimizing secondary metastasis by apoptosis of variety of cancer cells by a pattern of DNA fragmentation.

Yet another objective of the present invention is to provide a formulation comprising phytonutrients with natural chlorotoxins for arresting cancer cell growth.

Yet another objective of the present invention is to provide a formulation comprising phytonutrients with natural chlorotoxins for prevention of angiogenesis in cancer cells.

Yet another objective of the present invention is to provide a formulation comprising phytonutrients and natural chlorotoxins for regulating the process of phosphorylation that affects the p53 tumor suppressor protein leading to cell cycle arrest and apoptotic cell death.

Yet another objective of the present invention is to provide a formulation comprising phytonutrients and natural chlorotoxins for arresting the growth of cancer cell in the G1 phase of the cell cycle, changing in mitogenic signals specific to malignant cells and providing a universal effect on different forms of cancer.

Yet another objective of the present invention is to provide a formulation comprising phytonutrients and natural chlorotoxins for targeting cancer in humans, felines and canines, and other pet animals.

These and other aspects of the embodiments herein will be better appreciated and understood when considered in conjunction with the following description and the accompanying drawings. It should be understood, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

Other benefits and advantages of the present disclosure will be appreciated from the following detailed description.

BRIEF DESCRIPTION OF THE DRAWINGS

Exemplary embodiments of a system and method are shown in the accompanying drawings. The other objects, features, and advantages will occur to those skilled in the art from the following description of the preferred embodiment and the accompanying drawings in which:

FIG. 1 illustrates a flow chart explaining a method for synthesizing the formulation/composition comprising phytonutrients and natural chlorotoxins for targeting cancer, according to one embodiment of the present invention.

Although the specific features of the present invention are shown in some drawings and not in others. This is done for convenience only, as each feature may be combined with any or all of the other features in accordance with the present invention.

DETAILED DESCRIPTION OF INVENTION

The Definition of scorpion includes all of the following Scorpion families which includes by definition: Bothriuridae, Buthidae, Caraboctonidae Chactidae, Chaerilidae, Diplocentridae, Euscorpiidae, Gigantoscorpionidae, *Heterometrus swammerdami*, Hemiscorpiidae, Palaeopisthacanthidae, Pseudochactidae, Scorpionidae, Superstitioniidae, Typhlochactidae and Vaejovidae, and all Seventy-two scorpion species, belonging to Hemiscorpiidae.

In the following detailed description, reference is made to the accompanying drawings that form a part hereof, and in which the specific embodiments that may be practiced is shown by way of illustration. These embodiments are described in sufficient detail to enable those skilled in the art to practice the embodiments and it is to be understood that the logical, mechanical, and other changes may be made without departing from the scope of the embodiments. The following detailed description is therefore not to be taken in a limiting sense.

The various embodiments of the present invention provide a formulation/composition comprising phytonutrients and natural chlorotoxins for targeting cancer in humans, felines and canines, and other pet animals without any side effects. The embodiments of the present invention also provide a method for the synthesis of a formulation comprising phytonutrients and natural chlorotoxins for targeting cancer.

FIG. 1 illustrates a flow chart explaining a method for synthesizing the formulation/composition (RX002CxN) comprising phytonutrients and natural chlorotoxins such as Blue Scorpion Venom Chlorotoxin for targeting cancer, according to one embodiment of the present invention. The phytonutrients are selected from the group comprising of *Glycyrrizaglabra, Piper longum, Picrorhiza kurroa, Phyllanthus amarus, Bauhinia variegate*, and *Terminalia chebula*. The herbal raw material can also include *Cannabis sativa* (cannabinoids). The herbal raw materials are cleaned and dried and mixed together to form a uniform mixture. Then a coarse powder (101) is prepared such that it can pass through a 20-40 mesh size by either grinding or pulverizing using a suitable tool such as a mortar and pestle, or a processor such as a IKA Handheld Analytical Mill, or an IKA Continuous Feed Grinding machine EW-04300-30 with IKA 2836001 Continuous feed grinding drive. Then solvent comprising water/alcohol in a ratio 40:60 is added to the coarse powder mixture in a ratio 4-parts powder and 1-part solvent and the solvent is mixed thoroughly to obtain a homogeneous mixture (102). The mixture is macerated for at least 4 hours to 12 hours, followed by a cold extraction of 12 hours forming homogenous mixture (103). Cold extraction is achieved by taking the homogeneous mixture of solvent and phytonutrients powder and dissolving the mixture in warm water, and then rapidly cooling the mixture. The insoluble compounds precipitate out of the water, while the soluble ones stay dissolved. The solution can then be separated by reflux, filtration, or decantation. In the preferred method the mixture is refluxed (104) for 2 hours at 80° C. The addition of solvent maceration (105) and refluxing steps are repeated a minimum three times and sufficient quantity of solvent is added, if required. The residue is checked (106) for complete extraction after every refluxing step. The extract/residue is filtered and concentrated under vacuum (108). The extract/residue is vacuum tray dried at 70-80° C. for 12 hours (107). The extract/residue is scraped and the dried lumps of the extract/residue are milled (109). The natural chlorotoxin is added to the extract/residue and blended homogenously (110). The extract/residue is sieved and packed (111). The percentage yield is calculated according to the weight of the raw materials. The example utilizes the Blue Scorpion Venom Chlorotoxin venom however the opportunity to expand the viable chlorotoxin pool of compounds by utilizing any one of the more than 1004 known species of scorpion's in the treatment of disease's such as heart disease, cancer, Alzheimer's, epilepsy, inflammation and pain management is incorporate because any one of the vast number of scorpion's could be used as a donor animal and this specification includes the incorporation of any of these animals being used as an alternative sources of chlorotoxin's. For this example, the Blue Scorpion Venom Chlorotoxin venom is extracted by a mild electro-stimulation method that includes stimulating and scorpion restraining devices. However researchers have had success milking scorpions in the Buthidae family, the Scorpionidae family which includes the emperor scorpion (*Pandinus imperator*), and the *Heterometrus swammerdami* scorpion as well as specific species such as African *Androctonus australis, Hadrurus hirsutus*, Albino Scorpions, Black Scorpions or Asian Forest Scorpions, Blue Scorpions, Emperor Scorpions, Deathstalker Scorpions, Lesser Brown Scorpions, Red Claw Scorpions, Red Scorpions, Sand Scorpions, Tailless Whip Scorpions and Whip Scorpions. Many of these venoms have natural chlorotoxin that have shown indications as effective treatments for disease states such as cancer, Alzheimer's, epilepsy, inflammation and pain management. Scorpiones (Scorpions), Current records show that there are 1,004 species known which presents the researcher a wealth of chlorotoxins with which to analyze for effective treatments to disease states such as cancer, Alzheimer's, epilepsy, inflammation and pain management. The non-disulfide-bridged scorpion venom peptide has become a crucial substance to initiate pharmacologic activities including antibacterial, antifungal, antimalarial, antiviral and anticancer activities.

Specifically, for this example the Blue Scorpion Venom Chlorotoxin venom is extracted by mild Electro-stimulation method, that includes stimulating and scorpion restraining devices. To obtain the venom, the scorpion is subjected to an electrical current from a simple 12-volt battery or low voltage power supply such that the venoms are collected by the electrical stimulation method. Specifically, a series of regular currents are applied to shock the scorpion until the venom is ejected. For that purpose, controlling the scorpion is important, the scorpion is held with forceps by the tail and is then given a shock with electrode connected to the low voltage power source such as a battery or power supply. The venom droplet is recovered in a 1 ml vial after which the extracted venom kept frozen until used.

Then once the venom is extracted and frozen, the venom can be recovered from the freezing process using distilled water and centrifuged. The supernatant can then be lyophilized (freeze-dried), and maintained at −20° C. until used or the lyophilized powder can be added to the phytonutrients powder in the ratio of 1-part venom 10,000 parts by weight phytonutrients extract and mixing thoroughly. The extract from the residue is filtered and concentrated under vacuum. The extract from the residue is vacuum tray dried at 70-80° C. for 12 hours. The extract from the residue is scraped and the dried lumps of the extract from the residue are milled. The natural chlorotoxin is added to the extract/residue and blended homogenously. The extract/residue is sieved and packed. The percentage yield is calculated according to the weight of the raw materials.

The finished powder is made into a nutraceutical supplement in the form of pills that are taken by the patient. However, the final nutraceutical supplement could be formulated into a number of suitable delivery means such as, injectable, oral tablet, oral liquid, topical cream, nasal spray, dry powder aerosols, powder structures for water-soluble drugs, and powder containing time release capsules, since dry powder aerosols is the best route reported for chlorotoxin to cross the blood brain barrier and reach its site in cases of glioma this may be a preferred formulation. The pills can also contain any buffering or inorganic compounds suitable for the pill formation and that does not adversely affect the finished powder of phytonutrients extract and chlorotoxin powder. Typical excipients can be found in Table 1. All pharmaceutical formulations of the venom will be taken as a base in a suitable physiological vehicle to which the processed phytonutrient ingredients will be added and formulated with other inert excipients, stabilizers, and preservatives, as needed. The oral liquid and injectable formulations can be formed by taking the powder of phytonutrients extract and chlorotoxin powder and mixing it with a liquid, wherein the liquid is selected from the group consisting of deionized water, saline, plasma, and interstitial fluid, as well as stabilizers and preservatives, as needed.

The injectable formulations commonly use chemicals used in the production of vaccines. These include suspending fluid (sterile water, saline, or fluids containing protein); preservatives for example (Benzoic acid, salts, Sorbic acid, Parabens and paraben substitutes such as natural products such as "grape fruit seed", Benzyl Alcohol, Phenoxyethanol, Sodium Benzoate, Potassium Sorbate) and stabilizers (for example, albumin, phenols, and glycine); and adjuvants or enhancers that help improve the injectable effectiveness. The adjuvants can be selected from the group consisting of aluminum phosphate, aluminum hydroxide, Docosahexaenoic acid, and MF59, an immunologic adjuvant that uses squalene. The oral formulations utilize stabilizers selected from polyols, albumins and other proteins, surfactants, poloxamers, cyclodextrins and preservatives selected from Benzoic acid, salts, Sorbic acid, Parabens and paraben substitutes such as natural products such as "grape fruit seed", Benzyl Alcohol, Phenoxyethanol, Sodium Benzoate, Potassium Sorbate. The oral formulations utilize preservatives selected from the group Methyl, ethyl, propyl parabens sodium benzoate, benzoic acid, Methyl paraben/sodium benzoate, Benzyl Alcohol, Phenoxyethanol Sodium Benzoate, Potassium Sorbate and suitable combinations.

The pharmaceutical formulations of the present invention provide a formulation/composition comprising phytonutrients and natural chlorotoxins for targeting cancer in humans, felines and canines, and other pet animals, without any side effects.

Table 1 below illustrates the composition of the formulation/composition comprising phytonutrients and natural chlorotoxins for targeting cancer, Alzheimer's, epilepsy and pain management and excipients that can be utilized in the instant invention:

TABLE 1

| Sl No | Name of Phytonutrient | Derived from | % | Main function/ References |
|---|---|---|---|---|
| Pharmaceuticals actives | | | | |
| 1 | Glycyrrhizic acid | Glycyrrizaglabra | 13% | Anti-oxidant1 |
| 2 | Piperine | *Piper longum* | 0.54% | Bioavailability enhancer, 2 |
| 3 | Picroside & kuti koside | Picrorhhizakurroa | 15% | Hepatoprotective 3 |
| 4 | Tannins | *Phyllanthusamarus* | 55% | Anti-oxidant4 |
| 5 | | *Terminalia chebula* | 78% | |

TABLE 1-continued

| Sl No | Name of Phytonutrient | Derived from | % | Main function/ References |
|---|---|---|---|---|
| 6 | 36 amino acid peptide | Blue scorpion saliva | 0.01% | Anti-cancerous 5 |
| | | Excipients | | |
| 7 | Aqua Sucralose and citric acid. | | | Diluting agent |
| 8 | Sorbitol | | | |
| 9 | Glycerine | | | |
| 10 | Sodium benzoate | | | Preservatives |
| 11 | Na CMC | | | |
| 12 | Honey | | | Sweetener |
| 13 | Sucralose | | | Sweetener |
| 14 | Citric acid | | | Excipient |
| 15 | Water | | | Diluting agent |

According to one embodiment of the present invention, Bauhinia variegata bark extract is extracted in hydro-alcohol and used in the anti-cancer composition/formulation. Traditional literature states that, the Bauhinia variegata bark is used in worm infestation, scrofula, cervical lymphadenitis, and wounds. The Bauhinia variegata bark has antimicrobial and wound healing properties. In the phytoceutical approach, hydro-alcohol extract comprises quercitroside, Kaempferol-3-glucoside, lupeol and beta-sitosterolisoquercitroside, rutosidemyricetol glycoside, and Kaempferol glycosides. Stem extracts of Bauhinia variegata comprise phenanthraquinone, 2,7-dimethoxy-3-methyl-9,10 dihydrophenanthrene-1-4, dione (Bauhinione). The extracts from Bauhinia variegate find application in various inflammatory conditions, diabetes, chronic hyperglycemia, antitumor, and cytotoxic activity.

According to one embodiment of the present invention, the main compounds present in the anti-cancer formulation or composition (RX002CxN) are the 'phyto-complex with natural chlorotoxins.' The phyto-complex comprises the extracts of Glycyrrizaglabra, Piper longum, Picrorhiza kurroa, Phyllanthus amarus, Bauhinia variegate, and Terminalia chebula, in predetermined amounts. The chlorotoxins used in the composition are derived from the polypeptide of the blue scorpion saliva. This 'phyto-complex with natural chlorotoxins' act as a potent anti-cancer composition and is active against multi-focal oncological usages with special attention of cancers of blood, bone, colon, cervix, bladder, ovary, breast, prostate, and uterus.

According to one embodiment of the present invention, the following are methods of in vitro assay for anti-cancerous activity of the formulation/composition comprising phytonutrients and natural chlorotoxins for targeting cancer:

Example-1

Sulforhodomine B (SRB) Assay

The experimental procedure for SRB Assay is adopted for analyzing the anti-cancerous activity of the formulation/composition (RX002CxN). The dose response parameters are calculated for each test article. The growth inhibition of 50% (GI 50) is calculated from $(Ti-Tz)/(C-Tz) \times 100 = 50$, which is the drug concentration resulting in a 50% reduction in the drug incubation. The drug concentration resulting in total growth inhibition (TGI) is calculated from $Ti=Tz$. The Lc50 indicating net loss of cells following treatment is calculated from $[(Ti-Tz)/Tz] \times 100 = -50$. The values are calculated for each of these three (3) parameters if the level of activity was reached, however, if the effect is not reached or is exceeded, the values for that parameter are expressed as greater or less than the maximum or minimum concentration tested.

Following are the steps in the SRB assay protocol:
a. Preparation of the drug solutions: Confirming the test substance and number with "Form A" whenever a new drug received.
b. Test substance is stored based on the criteria and checked.
c. If the molecular weight of test substance is not known, prepare the working solution of the drug (10, 20, 40, 80 microgram/ml) with a specified vehicle.
d. If the molecular weight of the test substance is known, then prepare the working solution of the drug $10^{-7}$, $10^{-6}$, $10^{-5}$, $10^{-4}$ M concentration with the specified vehicle.
e. The working stock of the drug is prepared in appropriate solvent and further dilutions are made as per Table 1 below:

| Drug Concentration well | | µL of the working stock | | µL of the MiLLI-Q water | | Total volume µL | | µL Volume to be Added to the well | |
|---|---|---|---|---|---|---|---|---|---|
| µg/ml | Molar concentration | A | B | A | B | A | B | A | B |
| 10 | $10^{-7}$ | 10 | 1 | 90 | 999 | 100 | 1000 | 10 | 10 |
| 20 | $10^{-6}$ | 20 | 10 | 80 | 990 | 100 | 1000 | 10 | 10 |
| 40 | $10^{-5}$ | 40 | 100 | 60 | 900 | 100 | 1000 | 10 | 10 |
| 80 | $10^{-4}$ | 80 | 1000 | 20 | 00 | 100 | 1000 | 10 | 10 | f. Prepare the same concentrations of the test substance (the formulation or composition) for the vehicle control and also for the positive control.
g. Prepare for the culture plate preparation and drug or composition addition with single cell suspension of the required cell line grown in tissue, followed by counting of cells. The cell count is adjusted according to titration readings, each test substance (composition) is tested in 96 well plates with its four (4) dilutions in triplicate. The culture plates are incubated at 37° C. in carbon dioxide incubator for 24 hours. The drugs with dilutions −10, −20, −40, −80 µL are made in triplicate and accordingly culture plates are labeled as:
VC: Vehicle Control
PC: Positive Control
h. The culture plates are labeled and incubated for 48 hours. Experiment is terminated by gently layering the cells in the wells with 50 ml of chilled 30% TCA—in case of adherent cells and 50% TCA—in case the suspension cell lines for cell fixation. The culture plates are refrigerated at 4° C. for an hour. The culture pates are washed thoroughly with tap water at least five (5) times and air dried.
i. The culture plates are stained with 50 µL of 0.4% SRB for 20 minutes. The culture plates are washed with 1% acetic acid at least five (5) times and air dried. The bound SRB is eluted with 100 μL of Tris buffer for 10 minutes on a shaker. The absorbance is read in the micro titer reader at 540 nm with reference of 690 nm. The optical density of drug treated cells is compared with that of control cells and the growth inhibition is calculated at % values.

j. The anti-cancer potential of the formulation/composition (RX002CxN) comprising phytonutrients from phytonutrients bearing plants and natural chlorotoxins for targeting cancer is established through in vivo test or PK/PD study design. The absorption of formulation/composition RX002CxN starts in the duodenum, the first section of the small intestine in higher vertebrates. The peptides, proteins, and minerals present in the formulation/composition RX002CxN are absorbed completely by the human body, within 30 minutes. The main compound in the formulation/composition RX002CxN is a peptide comprising 36 amino acids along with flavonoids. The peptide comprising 36 amino acids pass the blood brain barrier and inhibits glioma cell invasion. The 36 amino acid peptide in the formulation/composition RX002CxN has a cumulative effect, within 24 hours.

Example-2

Activity Criteria

The inhibitory concentration (IC50) for synthetic compounds/formulations is typically ≤10 μg/ml or ≤$10^{-5}$M. The inhibitory concentration (IC50) for natural products or plant extracts typically is IC50≤20 mg/ml, and at any given point concentration, % growth inhibition ≥50 indicates activity.

Table 2 below illustrates the cell lines and the tissue of origin from which the cell lines are derived:

| Sr Nos | Name of the cell line | Tissues of origin |
|---|---|---|
| 1 | Colo 205 | Colon |
| 2 | Hop62 | Lung |
| 3 | HT29 | Colon |
| 4 | SiHa | Cervix |
| 5 | MIAPACA 2 | Pancreas |
| 6 | DWD | Oral |
| 7 | T24 | Bladder |
| 8 | PC3 | Prostate |
| 9 | A549 | Lung |
| 10 | ZR 75 1 | Breast |
| 11 | A2780 | Ovary |
| 12 | DU145 | Prostate |
| 13 | MCF7 | Breast |
| 14 | K562 | Leukemia |

According to one embodiment of the present invention, the drug development stages (formulation/composition) are carried out in the following stages:

Drug Discovery: Drug discovery begins with target identification-choosing a biochemical mechanism involved in a disease condition. The drug/composition/formulation candidates, discovered in academic and pharmaceutical/biotech research labs, are tested for their interaction with the drug target. Up to 5,000 to 10,000 molecules for each potential drug candidate are subjected to a rigorous screening process that includes functional genomics and/or proteomics, as well as other screening methods. After the researchers/scientists confirm interaction of the drug/composition with a target, the target is validated by checking for drug/composition activity versus the disease condition for which the drug/composition is being developed. After careful review, one or more lead compounds are chosen.

Ideation: This stage is primitive and creates and idea for how to lead with drug trials.

Target identification: This stage deals with how to fix the target, molecules, and precursors.

Product Characterization: When the candidate molecule shows promise as a therapeutic, it must be characterized; the molecule's size, shape, strengths and weaknesses, preferred conditions for maintaining function, toxicity, bioactivity, and bioavailability must be determined. Characterization studies will undergo analytical method development and validation. Early stage pharmacology studies help to characterize the underlying mechanism of action of the compound, including phytoceuticals.

Formulation, Delivery, Packaging Development: Drug developers must devise a formulation that ensures the proper drug delivery parameters. It is critical to begin looking ahead to clinical trials at this phase of the drug development process. Drug formulation and delivery may be refined continuously until, and even after, the drug's final approval. Scientists determine the drug's stability in the formulation itself, and for all the parameters involved with storage and shipment, such as heat, light, and time. The formulation must remain potent and sterile; and it must also remain safe (nontoxic). It may also be necessary to perform leachable on containers or packaging.

Pharmacokinetics and Drug Disposition: Pharmacokinetic (PK) and ADME (Absorption/Distribution/Metabolism/Excretion) studies provide useful feedback for formulation scientists. PK studies yield parameters such as AUC (area under the curve), Cmax (maximum concentration of the drug in blood), and Tmax (time at which Cmax is reached). Later on, this data from animal PK studies is compared to data from early stage clinical trials to check the predictive power of animal models.

Preclinical Toxicology Testing and IND Application: Preclinical testing analyzes the bioactivity, safety, and efficacy of the formulated drug product. This testing is critical to a drug's eventual success and as such, is scrutinized by many regulatory entities. During the preclinical stage of the development process, plans for clinical trials and an Investigational New Drug (IND) application are prepared. Studies taking place during the preclinical stage should be designed to support the clinical studies that will follow.

The main stages of preclinical toxicology testing are:

Acute Studies—Acute toxicology (tox) studies analyze the effects of one or more doses administered over a period of up to 24 hours. The aim of acute tox studies is to determine toxic dose levels and observe clinical indications of toxicity. Usually, at least two mammalian species are tested. Data from acute tox studies help determine doses for repeated dose studies in animals and Phase I clinical trials in humans.

Repeated Dose Studies—Depending on the duration of the studies, repeated dose studies may be referred to as subacute, subchronic, or chronic. The specific duration should anticipate the length of the clinical trial that will be conducted on the new drug. Again, two species are typically required.

Genetic Toxicity Studies—These studies assess the likelihood that a drug compound is mutagenic or carcinogenic. Procedures such as the Ames Test (conducted in bacteria) detect genetic changes. DNA damage is assessed in tests using mammalian cells such as the Mouse Micronucleus Test. The Chromosomal Aberration Test and similar procedures detect damage at the chromosomal level.

Reproductive Toxicity Studies—Segment I reproductive fox studies analyze the effects of the drug on fertility. Segment II and III studies detect effects on embryonic and post-natal development. In general, reproductive tox studies must be completed before a drug can be administered to women of child-bearing age.

Carcinogenicity Studies—Carcinogenicity studies are usually needed only for drugs intended for chronic or recurring conditions. They are time consuming and expensive, and must be planned for early in the preclinical testing process.

Toxicokinetic Studies—These are typically similar in design to PK/ADME studies except that they use much higher dose levels. They examine the effects of toxic doses of the drug and help estimate the clinical margin of safety. There are numerous FDA and ICH guidelines that give a wealth of detail on the different types of preclinical toxicology studies and the appropriate timing for them relative to IND and NDA or BLA filings.

Bioanalytical Testing: Bioanalytical laboratory work and bioanalytical method development supports most of the other activities in the drug development process. The bioanalytical work is key to proper characterization of the molecule, assay development, developing optimal methods for cell culture or fermentation, determining process yields, and providing quality assurance and quality control for the entire development process. It is also critical for supporting preclinical toxicology/pharmacology testing and clinical trials.

Clinical Trials: Clinical studies are grouped according to their objective into three types or phases:

Phase I Clinical Development (Human Pharmacology)—Phase I studies are used to evaluate pharmacokinetic parameters, tolerance and safety, generally in healthy volunteers. These studies include initial single-dose studies, dose escalation and short-term repeated-dose studies.

Phase II Clinical Development (Therapeutic Exploratory)—Phase II clinical studies are small-scale trials to evaluate a drug's preliminary efficacy and side effect profile. Additional safety and clinical pharmacology studies are also included in this category.

Phase III Clinical Development (Therapeutic Confirmatory)—Phase III studies are large-scale clinical trials for safety and efficacy in large patient populations. While phase III studies are in progress, preparations are made for submitting the Biologics License Application (BLA), filing under the FDA Nutraceutical Act or the New Drug Application (NDA).

The foregoing description of the specific embodiments will so fully reveal the general nature of the embodiments herein that others can, by applying current knowledge, readily modifying and/or adapting for various applications, such specific embodiments, without departing from the generic concept, and, therefore, such adaptations and modifications should and are intended to be comprehended within the meaning and range of equivalents of the disclosed embodiments.

It is to be understood that the phraseology or terminology employed herein is the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the embodiments herein with modifications. The scope of the embodiments will be ascertained by the claims to be submitted at the time of filing a complete specification.

Advantages of the Invention

The embodiments of the present invention provide a formulation comprising phytonutrients from phytonutrient-bearing plants and natural chlorotoxins for targeting cancer, infection, inflammation, and pain, without any side effects.

The embodiments of the present invention provide a method for the synthesis of a formulation comprising phytonutrients from phytonutrient-bearing plants and natural chlorotoxins for targeting cancer, infection, inflammation, and pain.

The embodiments of the present invention provide a formulation comprising phytonutrients and natural chlorotoxins for minimizing tumor growth.

The embodiments of the present invention provide a formulation comprising phytonutrients from phytonutrient-bearing plants and natural chlorotoxins for minimizing secondary metastasis by apoptosis of variety of cancer cells by a pattern of DNA fragmentation.

The embodiments of the present invention provide a formulation comprising phytonutrients from phytonutrients bearing plants and natural chlorotoxins for arresting cancer cell growth.

The embodiments of the present invention provide a formulation comprising phytonutrients from phytonutrient-bearing plants and natural chlorotoxins for prevention of angiogenesis in cancer cells.

The embodiments of the present invention provide a formulation comprising phytonutrients from phytonutrient-bearing plants and natural chlorotoxins for regulating the process of phosphorylation that affects the p53 tumor suppressor protein leading to cell cycle arrest and apoptotic cell death.

The embodiments of the present invention provide a formulation comprising phytonutrients from phytonutrient-bearing plants and natural chlorotoxins for arresting the growth of cancer cell in the G1 phase of the cell cycle, changing in mitogenic signals specific to malignant cells, and providing a universal effect on different forms of cancer.

The pharmaceutical formulations of the present invention provide a formulation/composition comprising phytonutrients and natural chlorotoxins for targeting cancer, infection, inflammation and pain in humans, felines and canines, and other pet animals without any side effects.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the embodiments herein with modifications. The scope of the embodiments will be ascertained by the claims to be submitted at the time of filing a complete specification.

It should be understood that the foregoing description is only illustrative of the invention. Various alternatives and modifications can be devised by those skilled in the art having the benefit of this disclosure, without departing from the invention. Accordingly, the invention is intended to embrace all such alternatives, modifications and variances.

Certain exemplary embodiments of the disclosure may be described. Of course, the embodiments may be modified in form and content, and are not exhaustive, i.e., additional aspects of the disclosure, as well as additional embodiments, will be understood and may be set forth in view of the description herein. Further, while the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but, not both" then the term "only A or B but not both" will be employed. Thus, use of the term "or" herein is the inclusive, and not the exclusive use. See, Bryan A. Garner, A Dictionary of Modern Legal Usage 624 (2d, Ed. 1995). Also, to the extent that the terms "in" or "into" are used in the specification or the claims, it is intended to additionally mean "on" or "onto." Furthermore to the extent the term "connect" is used in the specification or claims, it is intended to mean not only "directly connected to," but also "indirectly connected to" such as connected through another component or components.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus and method, and illustrative examples shown and described. Accordingly, departures may be made from such details without departing from the spirit or scope of the applicant's general inventive concept.

We claim:

1. A method for the synthesis of a nutraceutical supplement comprising phytonutrients and natural chlorotoxins for targeting disease comprising of:
   A. First creating a powder from said phytonutrients comprising of the steps:
      a. Forming a first phytonutrients powder from plants comprising said phytonutrients, wherein said plants are selected from the group consisting of *Glycyrriza glabra, Piper longum, Picrorhhiza kurroa, Phyllanthus amarus, Bauhinia variegata, Terminalia chebulain*, and combinations thereof;
  - b. Applying a solvent to said first phytonutrients powder to form a first mixture;
  - c. Macerating said first mixture;
  - d. Separating the soluble compounds in said first mixture using cold extraction;
  - e. Separating said soluble compounds from the said first mixture into a first residue and first soluble compounds;
  - f. Applying a solvent to said first residue to form a second mixture;
  - g. Macerating said second mixture;
  - h. Separating the soluble compounds in said second mixture using cold extraction;
  - i. Separating said soluble compounds from the said second mixture into a second residue and second soluble compounds;
  - j. Applying a solvent to said second residue to form to form a third mixture;
  - k. Macerating said third mixture;
  - I. Separating the soluble compounds in said third mixture using cold extraction;
  - m. Separating said soluble compounds from the said third mixture into third residue and soluble compounds;
  - n. Concentrating said third residue by filtering and concentrated under vacuum to create an extract;
  - o. Drying said extract;
  - p. Milling said extract into a second phytonutrients powder;
- B. Second, extracting chlorotoxins from the venom of a scorpion comprising of:
  - a. Securely holding the scorpion;
  - b. Applying an electrical stimulus to said scorpion;
  - c. Collecting the venom containing the chlorotoxins in a 1 ml vial;
  - d. Freezing said venom;
  - e. Taking the frozen venom and forming a supernatant using distilled water;
  - f. Lyophilizing said supernatant to form a lyophilized chlorotoxins powder containing chlorotoxins;
- C. Third, adding 0.0001 grams of the lyophilized powder containing chlorotoxins to 1 gram of said phytonutrients powder to form a chlorotoxins and phytonutrients powder;
- D. Fourth, mixing said chlorotoxins and phytonutrients powder to form a uniform powder mixture of phytonutrients and chlorotoxins;
- E. Fifth, taking said uniform powder mixture of phytonutrients and chlorotoxins and mixing an effective amount thereof with at least one excipient to formulate said nutraceutical supplement.

2. The method of claim 1, wherein the disease is selected from the group consisting of cancer, Alzheimer's, heart disease, epilepsy, and pain management.

3. The method of claim 1, wherein the chlorotoxins are from venom extractions from a Blue Scorpion.

4. The method of claim 1, wherein the chlorotoxins are collected from the scorpion species selected from the group consisting of *Bothriuridae, Buthidae, Caraboctonidae, Chactidae, Chaerilidae, Diplocentridae, Euscorpiidae, Gigantoscorpionidae, Heterometrus swammerdami, Hemiscorpiidae, Palaeopisthacanthidae, Pseudochactidae, Scorpionidae, Superstitioniidae, Typhlochactidae, Vaejovidae*, African *Androctonus australis, Hadrurus hirsutus*, Albino Scorpions, Black Scorpions, Asian Forest Scorpions, Blue Scorpions, Emperor Scorpions, Deathstalker Scorpions, Lesser Brown Scorpions, Red Claw Scorpions, Red Scorpions, Sand Scorpions, Tailless Whip Scorpions, and Whip Scorpions.

5. The method of claim 1, wherein said excipient is selected from the group consisting of water, aqua, sorbitol, glycerin, sodium benzoate, sodium carboxymethylcellulose (Na-CMC), honey, sucralose and citric acid.

6. The method of claim 1, wherein one or more of said solvents comprises a water:alcohol ratio of 40:60.

7. The method of claim 1, further comprising forming the nutraceutical supplement into a physiological vehicle, wherein said physiological vehicle is selected from the group consisting of a pill, an injectable liquid, an oral liquid, an oral tablet, a topical cream, a nasal spray, and a dry powder aerosol.

8. The method of claim 7, wherein the said injectable liquid is formed by mixing the nutraceutical supplement with amounts of suspending liquid, stabilizers, and preservatives.

9. The method of claim 8, wherein the suspending liquid is selected from the group consisting of deionized water, saline, plasma, and interstitial fluid.

10. The method of claim 8, wherein the preservatives are dissolved in said suspending liquid and said preservatives are selected from the group consisting of benzoic acid, salts, sorbic acid, paraben substitute, grape fruit seed, benzyl alcohol, phenoxyethanol, sodium benzoate, potassium sorbate, and parabens.

11. The method of claim 8, wherein the stabilizers are dissolved in said suspending liquid and said stabilizers are selected from the group consisting of albumin, proteins, phenols, polyols, glycine, poloxamers, and cyclodextrins.

12. The method of claim 7, wherein the physiological vehicle is a pill which is formulated by mixing the nutraceutical supplement with amounts of adjuvants, excipients, stabilizers, and preservatives.

13. The method of claim 12, wherein said excipient is selected from the group consisting of water, aqua, sorbitol, glycerin, sodium benzoate, sodium carboxymethylcellulose (Na-CMC), honey, sucralose, and citric acid.

14. The method of claim 13, wherein said adjuvants are selected from the group consisting of aluminum phosphate, aluminum hydroxide, docosahexaenoic acid, and MF59.

15. The method of claim 7, wherein the oral liquid is formed by mixing the nutraceutical supplement with amounts of liquid, stabilizer, and preservatives.

16. The method of claim 15, wherein the liquid is selected from the group consisting of deionized water, saline, plasma, and interstitial fluid.

17. The method of claim 15, wherein the stabilizer is selected from the group consisting of polyols, albumins and other proteins, surfactants, poloxamers, cyclodextrins and the preservatives are selected from benzoic acid, salts, sorbic acid, paraben substitute, grape fruit seed, benzyl alcohol, phenoxyethanol, sodium benzoate, potassium sorbate and parabens.

18. The method of claim 15, wherein the preservatives are selected from the group consisting of methyl-, ethyl-, and propyl-parabens, sodium benzoate, benzoic acid, methyl paraben/sodium benzoate, benzyl alcohol, phenoxyethanol, grape fruit seed, potassium sorbate, and parabens.

* * * * *